(12) United States Patent
Lavi et al.

(10) Patent No.: US 12,285,191 B2
(45) Date of Patent: Apr. 29, 2025

(54) POINT AND CLICK ALIGNMENT METHOD FOR ORTHOPEDIC SURGEONS, AND SURGICAL AND CLINICAL ACCESSORIES AND DEVICES

(71) Applicant: Orthex, LLC, Warsaw, IN (US)

(72) Inventors: Abraham Lavi, Delray Beach, FL (US); Dror Paley, West Palm Beach, FL (US)

(73) Assignee: Orthex, LLC, Warsaw, IN (US)

( * ) Notice: Subject to any disclaimer, the term of this patent is extended or adjusted under 35 U.S.C. 154(b) by 220 days.

(21) Appl. No.: 17/750,303

(22) Filed: May 21, 2022

(65) Prior Publication Data

US 2022/0273341 A1    Sep. 1, 2022

Related U.S. Application Data

(60) Continuation of application No. 16/291,452, filed on Mar. 4, 2019, now Pat. No. 11,337,732, which is a division of application No. 14/499,536, filed on Sep. 29, 2014, now Pat. No. 10,258,377.

(60) Provisional application No. 61/883,492, filed on Sep. 27, 2013.

(51) Int. Cl.
| | | |
|---|---|---|
| *A61B 17/62* | (2006.01) | |
| *A61B 17/66* | (2006.01) | |
| *A61B 34/10* | (2016.01) | |
| *G06F 3/04847* | (2022.01) | |
| *G16H 20/40* | (2018.01) | |
| *G16H 30/40* | (2018.01) | |
| *G16H 40/63* | (2018.01) | |

(52) U.S. Cl.
CPC .............. *A61B 17/62* (2013.01); *A61B 17/66* (2013.01); *A61B 34/10* (2016.02); *G06F 3/04847* (2013.01); *G16H 20/40* (2018.01); *G16H 30/40* (2018.01); *G16H 40/63* (2018.01); *A61B 2034/105* (2016.02); *A61B 2034/108* (2016.02)

(58) Field of Classification Search
CPC ................................. A61B 17/62; A61B 17/66
See application file for complete search history.

(56) References Cited

U.S. PATENT DOCUMENTS

| | | | |
|---|---|---|---|
| 5,552,883 A | | 9/1996 | Busch-Vishniac et al. |
| 5,797,908 A | * | 8/1998 | Meyers .............. A61B 17/6441 606/56 |
| 5,863,292 A | * | 1/1999 | Tosic ................. A61B 17/6441 606/56 |

(Continued)

*Primary Examiner* — Nicholas J Plionis
(74) *Attorney, Agent, or Firm* — Gerald W. Roberts; John V. Daniluck; Dentons Bingham Greenebaum LLP

(57) ABSTRACT

The invention is a point and click method for positioning an external fixator on a patient, in which a surgeon—using a computer mouse or similar device—inscribes lines or points on a computer screen displaying an x-ray or other photographic image of the bones of a patient together with two rings in position adjacent the bones. By inscribing lines on the computer screen, the underlying drawings program detects the x-y coordinates of any point on the screen when the user (the surgeon or other practitioner) clicks on it, and outputs the x-y coordinates of every point identified by the user including the two points defining any desired line. The practitioner thus can, using "point and click" operation, govern the repositioning of two fixator rings on the bones of a patient.

4 Claims, 14 Drawing Sheets

Proximal

(56) References Cited

U.S. PATENT DOCUMENTS

| | | | | |
|---|---|---|---|---|
| 6,129,727 | A * | 10/2000 | Austin | A61B 17/62 606/56 |
| 2006/0235384 | A1 * | 10/2006 | Rovesti | A61B 17/62 606/56 |
| 2010/0179548 | A1 * | 7/2010 | Marin | A61B 17/62 606/54 |
| 2010/0312243 | A1 * | 12/2010 | Ross | A61B 17/64 606/56 |
| 2011/0034963 | A1 * | 2/2011 | Bagnasco | A61B 17/6425 606/86 R |
| 2011/0082458 | A1 * | 4/2011 | Crozet | A61B 17/62 606/54 |
| 2012/0078251 | A1 * | 3/2012 | Benenati | A61B 17/6425 606/56 |
| 2012/0232554 | A1 * | 9/2012 | Shaevitz | A61B 17/62 606/56 |
| 2012/0330312 | A1 * | 12/2012 | Burgherr | A61B 17/66 606/54 |
| 2014/0276821 | A1 * | 9/2014 | Murray | A61B 17/62 606/57 |

* cited by examiner $$Slope = m_{p1} = \frac{(z_8 - z_7)}{(x_8 - x_7)} \quad angle = \lambda_{p1} = tan^{-1}(m_{p1})$$

$$Slope = m_{p2} = \frac{(z_2 - z_1)}{(x_2 - x_1)} \quad angle = \lambda_{p2} = tan^{-1}(m_{p2})$$

$$Slope = m_{d2} = \frac{(z_5 - z_4)}{(x_5 - x_4)} \quad angle = \lambda_{d2} = tan^{-1}(m_{d2})$$

$$Slope = m_{d1} = \frac{(z_9 - z_{10})}{(x_9 - x_{10})} \quad angle = \lambda_{d1} = tan^{-1}(m_{d1})$$

Ball machined out of Same material block

Extended shaft to accept "ball"

POINT AND CLICK ALIGNMENT METHOD FOR ORTHOPEDIC SURGEONS, AND SURGICAL AND CLINICAL ACCESSORIES AND DEVICES

CROSS-REFERENCE TO RELATED APPLICATIONS

The present application is a continuation of U.S. patent application Ser. No. 16/291,452, filed Mar. 4, 2019, which is a division of U.S. patent application Ser. No. 14/499,536, filed Sep. 29, 2014, which claims priority to U.S. Provisional Patent Application No. 61/883,492 filed Sep. 27, 2013, all of which are incorporated herein by reference.

BACKGROUND OF THE INVENTION

The invention pertains to simple and effective ways to extract and wield alignment data from x-ray or other photographic images for the automated repositioning of external fixators, as needed to align bones during the healing process. In previous uses of external fixators for orthopedic bone alignment and correction, a wide variety of techniques have been used to assist the surgeon in positioning or repositioning the bones using an external fixator. In other words, unlike internal fixation such as screws, plates and intramedullary nails, external fixators provide postoperative adjustability—and there are many ways to make such adjustments. In the situation of limb lengthening, trauma, or deformity correction, gradual manipulation is necessary and possible with frame adjustment. For the most part, postoperative adjustment with external fixators, particularly external ring fixators, has been a manual undertaking, and although the surgeon is generally guided by x-rays or other imaging showing the relative positions of the bones, the calculations of the magnitude of linear translation and angular rotation to affect the adjustment have generally been made by eye and experience. While experience counts for a great deal in health care in general and orthopedics in particular, an automated external fixator ring adjustment system may enhance the surgical outcome directly or indirectly by reducing human error. Automated adjustment based on the x-ray or other imaging, can reduce guesswork, or simplify the manual calculations on the part of the surgeon or other healthcare provider. Going a step further, automating the adjustment process has the potential of manipulating the external fixator without relying on the patient.

SUMMARY OF THE INVENTION

In order to meet this need, the present invention is a point-and-click (P&C) method in which the surgeon, using a computer mouse or similar device, inscribes lines or points on a computer screen displaying an x-ray or other photographic images of the bones and the two rings attached to them. It is essential to secure two such images, one anterior-posterior (AP) view and the other lateral-medial (LM) view. By inscribing the lines on the computer screen, the drawing program detects the x-y coordinates of any point on the screen when the user clicks on it, and likewise detects the start and end of a line, and outputs the x-y coordinates of every point identified by the user including the two points defining any desired line. By the use of at least the AP and LM views, the algorithm extracts the coordinates for the positions of the pertinent points and lines on the images and produces the angular orientation of the bone segments, the angles that each ring makes relative the x, y, and z coordinates of the image, and the coordinates of the ring centers. In addition, the algorithm enables the surgeon to visualize the positioning of an osteotomy and the center of rotation point and angulation, or CORA, before actually performing an osteotomy. A feature of the computer algorithms disclosed herein enables the surgeon to evaluate different positions for the osteotomy and CORA, before any surgery and using only bone images, and to develop a practical sequence to bone rotation and translation to achieve surgical goals. The sequence of bone rotation and translation serves as the basis of the patient's treatment after surgery. Alternatively, the surgeon may forego such pre-op exploration and proceeds directly to the next step. The computer algorithms disclosed herein receives as input the coordinates of the points identified, through the P&C phase with the frame mounted on the patient, calculates and implements automatically the necessary adjustments in the ring positions, in both length and direction, to achieve the desired bone adjustment. The pre-op results, if any, form the basis for frame adjustment henceforward. The computer and specific algorithms can calculate—and even implement—the necessary adjustments by first establishing the three dimensional orientation of the bones and the fixator rings as shown in the images, and then by calculating the necessary three-dimensional adjustments to move the fixator rings and bones to the new desired position. This feature is feasible because data obtained from the two views, AP and LM, are used to evaluate lengths, linear translation values, and rotational angles magnitudes in three dimensions. One facilitating feature in providing adequate information in the x-ray or other image is the addition of (at least) three mechanical marker structures on each ring. The markers may be placed at any of the free holes or slots available on a ring. The mechanical marking can include anything from a knob, post, bolt, or other three-dimensional structure to an application of fluorescent or otherwise x-ray visible paint. These mechanical marker structures provide key orientation points in the x-ray or other images to allow the radiologist or orthopedic surgeon to understand how the three dimensional ring is positioned in the two-dimensional image as viewed on the computer screen.

DETAILED DESCRIPTION OF THE INVENTION

The benefits of external fixators, particularly external fixator rings, have been apparent for decades. Prior to the use of external fixators, the field of orthopedics faced an ongoing challenge in that external immobilization devices, including but not limited to plaster or Fiberglas casts, which did not provide adequate control of bone orientation during healing or realignment and provided no opportunity for gradual adjustment of bone position during the healing process. By contrast, reliance on permanent implants, including bone screws, may hinder natural bone healing without permanent prostheses and the attendant disadvantages thereof. With external fixators, the orthopedic surgeon obtains the best of both worlds of (temporary) bone prostheses and external immobilization or anchoring. By way of illustration, the pins and tensioned wires associated with the external fixator provide temporary bone alignment—with further continued immobilization or progressive adjustment as desired—and the external fixator ring itself provides a sufficient anchor and even protective structure to obviate the need for any traditional sort of cast.

The present invention is primarily useful for external fixator applications in which one or more bones are treated by surrounding them—and any other immediately associated anatomic structures—with two external fixator rings. Struts, typically six struts, connect the set of two fixator rings. A typical external fixator system suitable for use with the present invention is the design disclosed (as a non-limiting example) in U.S. Pat. No. 5,702,389, incorporated herein by reference. Pins, and wires under tension, anchored to the rings pass through the skin and surrounding tissue into the bones to be immobilized or adjusted. After temporary implantation of the pins, the rings and struts provide an adjustable anchor for moving or immobilizing the pins and the bone attached thereto as desired. When all bone healing is complete, the surgeon mechanically removes the rings and struts, and surgically removes the pins. After the relatively minor healing of the skin and tissue (where the pins and wires used to be) has occurred, the bones or joints involved are positioned as desired and bone union is achieved in the case of a fracture or osteotomy without a permanent implant and without the imprecision disadvantages of a traditional cast or splint.

Figure 2:
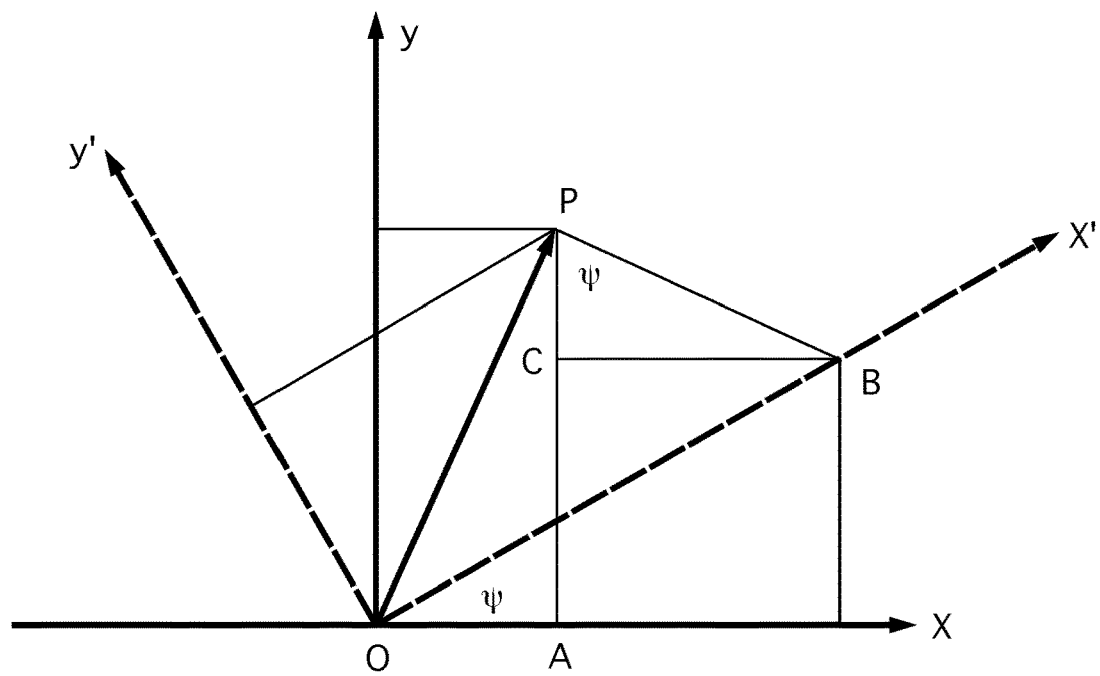
FIG. 2 is a line graph which illustrates the calculation of yaw around the z-axis.

Referring now to FIG. 2, and considering the first rotation (yaw) around the z-axis:

$$P = i'x' + j'y' + k'z' = ix + jy + kz$$

$$x = OA - BC = x' \cos \psi - y' \sin \psi$$

$$y = AB + PC = x' \sin \psi + y' \cos \psi$$

$$z = z'$$

We define the rotation matrix $R_z(\psi)$:

$$\begin{bmatrix} X \\ y \\ z \end{bmatrix} = R_z(\Psi) \begin{bmatrix} x' \\ y' \\ z' \end{bmatrix} \quad R_z(\Psi) = \begin{pmatrix} \cos(\Psi) & -\sin(\Psi) & 0 \\ \sin(\Psi) & \cos(\Psi) & 0 \\ 0 & 0 & 1 \end{pmatrix}$$

Similarly, if we consider the second rotation $\theta$ (pitch) around the y-axis we can show $$R_y(\theta) = \begin{pmatrix} \cos(\theta) & 0 & \sin(\theta) \\ 0 & 1 & 0 \\ -\sin(\theta) & 0 & \cos(\theta) \end{pmatrix}$$

And for the third rotation $\phi$ (roll) around the x-axis $$R_x(\phi) = \begin{pmatrix} 1 & 0 & 0 \\ 0 & \cos(\phi) & -\sin(\phi) \\ 0 & \sin(\phi) & \cos(\phi) \end{pmatrix}$$

The full rotation matrix of the Platform relative to the Base is:

$$^PR_B = R_z(\Psi) * R_y(\theta) * R_x(\phi) \quad (1)$$

$$^PR_B = \begin{bmatrix} \cos(\Psi)\cos(\theta) & -\sin(\Psi)\cos(\phi) + \cos(\Psi)\sin(\theta)\sin(\phi) & \sin(\Psi)\sin(\phi) + \cos(\Psi)\sin(\theta)\cos(\phi) \\ \sin(\Psi)\cos(\theta) & \cos(\Psi)\cos(\phi) + \sin(\Psi)\sin(\theta)\sin(\phi) & -\cos(\Psi)\sin(\phi) + \sin(\Psi)\sin(\theta)\cos(\phi) \\ -\sin(\theta) & \cos(\theta)\sin(\phi) & \cos(\theta)\cos(\phi) \end{bmatrix}$$

This is Equation 1. Note that the order of rotation produces a different $^PR_B$ transformation matrix and, consequently, different results.

Figure 3:
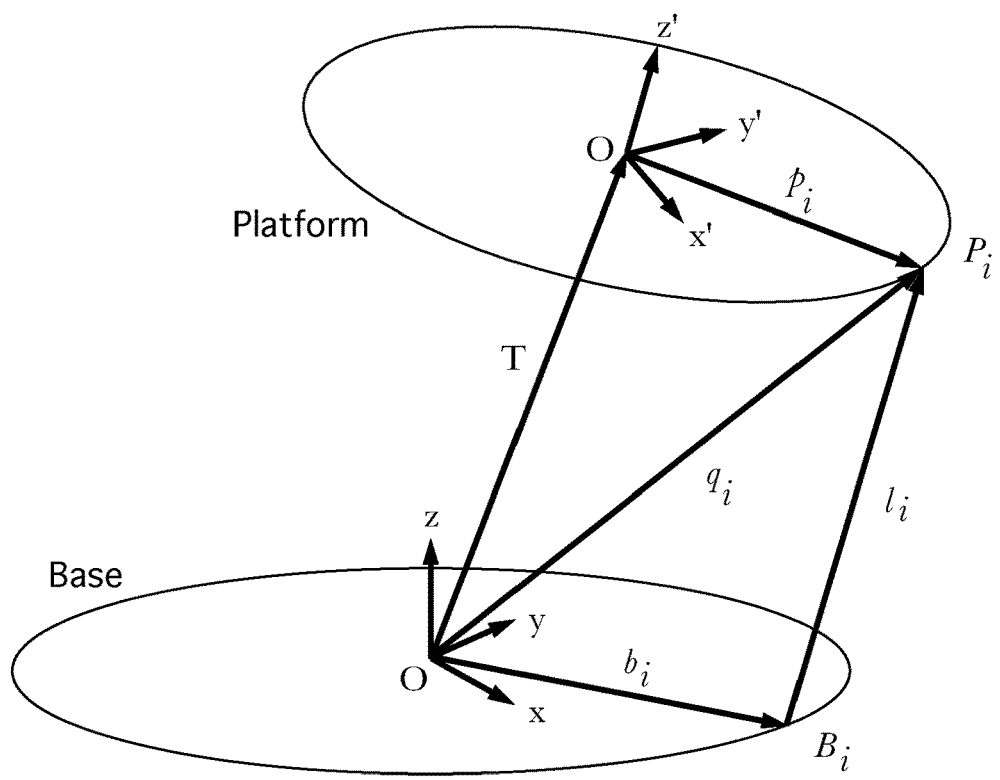
FIG. 3 is a schematic diagram superimposing line and angle definitions over two elliptical depictions of the platform ring and the base ring of the present invention.

Considering the above description of a basic Stewart Platform, and referring now to FIG. 3, of a traditional cast or splint.

Figure 1B:
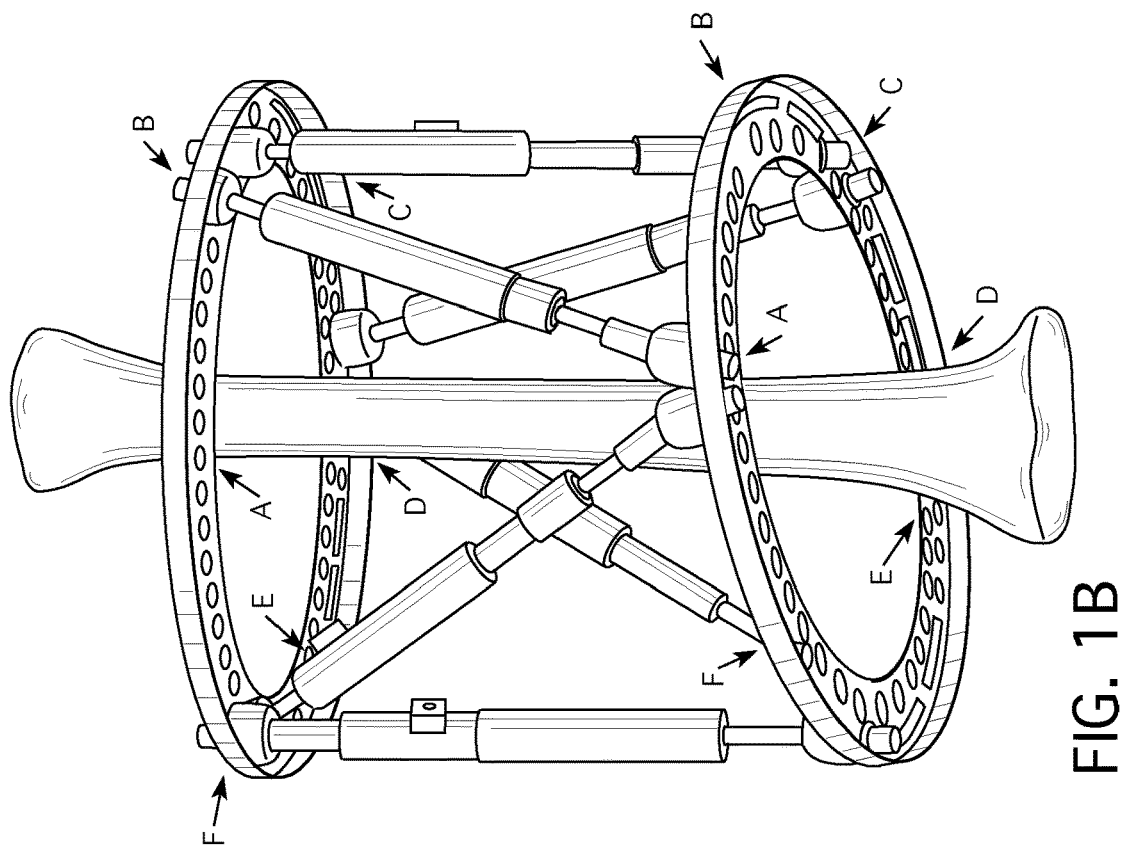
FIGS. 1A and 1B show in perspective view the ring fixators used in the present invention.
Figure 1A:
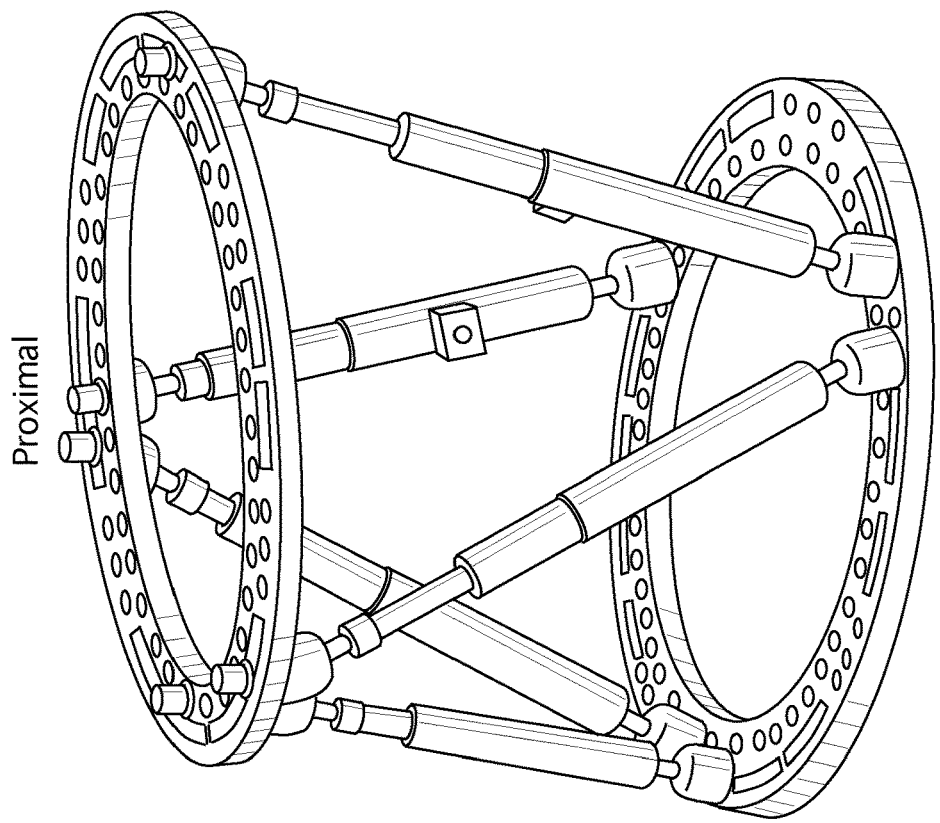

The present invention uses the innate geometry and kinematics involved in having an external fixator system in which two rings and all associated hardware can move in three dimensions. The invention deploys the basic geometry and kinematics in a proprietary algorithm and computerized device for displaying and optionally implementing the moving of the rings and associated hardware and bones to the position(s) either desired by the surgeon, calculated by the algorithm, or both. Therefore, a review of the applicable geometry and kinematics is useful. The Stewart Platform forms the basis of the external two-ring fixator used in orthopedics. In FIG. 1A, three pairs of adjustable-length struts oriented as shown connect two rings to form a frame. This structure constitutes the theoretical construct of a "Stewart Platform." In the following introductory explanation, the term Stewart Platform refers to the rings, which can move freely in all a three-dimensional (translation and rotation), because of the infinite length and angle variability provided by the struts.

The Stewart Platform consists of two rigid platforms (rings) connected by six variable length legs. The base ring is usually the reference framework, with orthogonal axes (x, y, z). The platform (or the second ring, generally positioned atop the base) has its own orthogonal coordinates (x', y', z'). The origin of the platform coordinates can be defined by three translational displacements with respect to the Base, one for each axis. Three angular displacements then define the orientation of the platform with respect to the Base. The platform therefore has six degrees of freedom with respect to the base. A set of Euler angles are used in the following sequence:

11. Rotate an angle ψ (yaw) around the z-axis
22. Rotate an angle θ (pitch) around the y-axis
33. Rotate an angle φ (roll) around the x-axis
the coordinates qi with respect to the Base reference framework of the anchor point $p_i$ of the $i^{th}$ leg are given by the equation:

$$q_i = T + R_B * p_i \quad (2)$$

where T is the translation vector, giving the positional linear displacement of the origin of the platform frame with respect to the Base reference framework, and $p_i$ is the vector defining the coordinates of the anchor point $P_i$ with respect to the platform framework. Similarly, the length of the $i^{th}$ leg is given by Equation 3, $$l_i = T + R_B * p_i - b_i \quad (3)$$

The vector bi is defines the coordinates of the lower anchor point Bi. These six equations give the lengths of the six legs to achieve the desired position and attitude of the platform. When considering the Forward Kinematics, this expression represents 18 simultaneous non-linear equations in the six unknowns representing the position and attitude of the platform. The solution of (x', y', z') coordinates and moving platform angles (ψ, θ, φ) from a set of six leg lengths is extremely challenging. The problem is further complicated because the solution is not unique. In other words for a set of Ii (i=1, . . . 6) numbers, there may be multiple (x', y', z') and (ψ, θ, φ) set of numbers and such set satisfy the 18 equations mentioned. This invention incorporates a new computer algorithm that employs a random search and mathematical optimization techniques and uses data extracted from the x-ray or other image in securing the unique solution to the 18—equation problem.

As important as external fixator technology has proven to be in the field of orthopedics, external fixators created certain challenges themselves. For example, an x-ray image of a body part—together with two external fixator rings, six struts, and the multiple pins (and tensioned wires) anchored on the rings and implanted through the skin into the bone—can be challenging to interpret because foreground hardware blocks other hardware positioned aft in any given x-ray view. In any x-ray viewed from any given angle, at least one attachment point of a strut to a ring will not be visible because the image of the bone or even the soft tissue that is interposed within the circumference of the rings may be the cause. Actually, in most two-ring six-strut external fixator applications, if an x-ray is truly normal to the anterior-posterior view and the frame is centered in the view, typically two of the strut attachment points in the foreground will obscure two attachment points in the background. In order to overcome this limitation, three or more visible markers are strategically placed around each ring. The markers assist in the interpretation of, and subsequent analysis of x-ray or other images of the rings, struts, pins and associated anatomic regions.

Referring now to FIG. 1A, a typical arrangement of two external fixator rings and six adjustable struts is shown in perspective view. The adjustable struts are adjustable as to their length, as shown using a telescoping design of the present invention. The pins (and tensioned wires), which are actually implanted into the patient bone through the skin, are not shown in FIG. 1A. FIG. 1B identifies tab positions, or attachment loci, on the rings. Each ring possesses six equidistant attachment loci A, B, C, D, E, and F. In a typical configuration, both the proximal and distal have the same ring design, and the struts connect to the proximal ring at positions A, C and E (say) and concomitantly connect to the distal ring at positions B, D and F—or vice versa.

For simplicity's sake, and as an initial illustration of the present invention and referring to FIG. 1B, presume that in a two-ring fixator application the proximal ring is connected to three pairs of adjustable struts at positions at attachment loci B, D and F. The distal ring is connected to the alternately conjoined ends of the same six struts in three strut pairs at attachment loci A, C and E. These attachment points as defined are shown in FIG. 1B. The invention then includes the addition of three separable markers on each ring. For example, two struts already occupy the two outer holes of Tab A and a fixation bolt may occupy the center hole. Because of the importance of this location, the first marker may be located in hole #2 of the inner row of holes of the ring, the second marker at the middle hole of Tab B, approximately 60° clockwise, and the third marker at the center of Tab C. However, in providing the previously mentioned example, the user will appreciate that the key is to add at least three visible markers to each ring and to know the position of each such marker. While there is no guarantee that all markers will be visible in any given x-ray, in part due to the presence of other hardware in the fixator application, the visibility of one or two markers in the x-ray will give orientation points to the viewer that can then be used to implement the present invention. The judicious selection of the marker positions is extremely important in insuring the visibility of the markers on the x-ray or other image of both AP and LM views. The marker positions influence the validity of the data secured from the P&C procedure.

Figure 4:
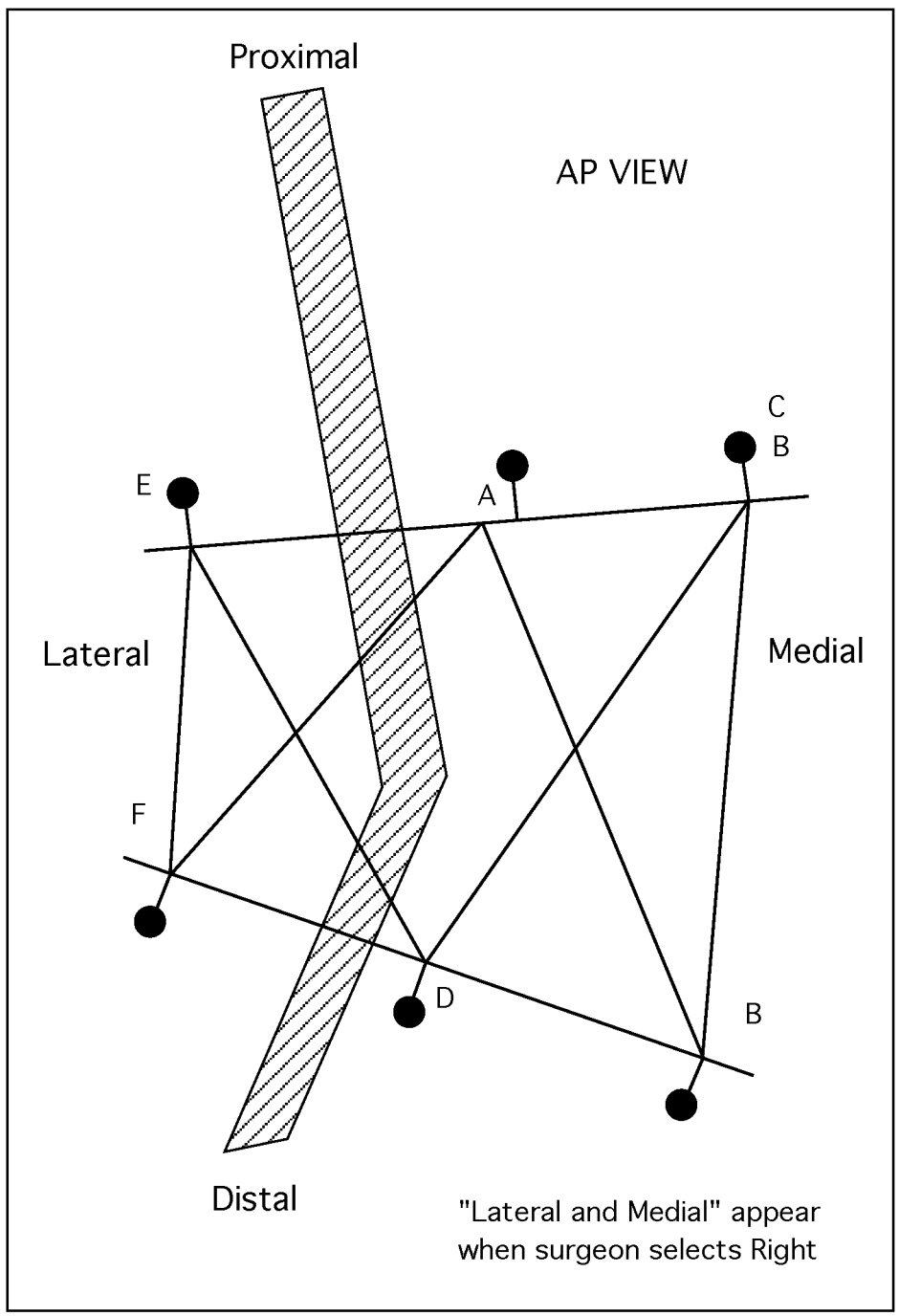
FIG. 4 is a schematic diagram of an idealized x-ray image displayed on a computer screen.
Figure 5:
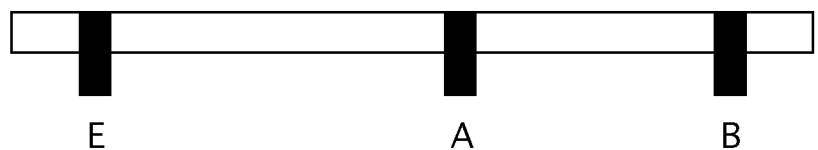
FIG. 5 is a plan view of rings, including AP Projection and LM Projection, of the present invention showing marker locations.
Figure 5:
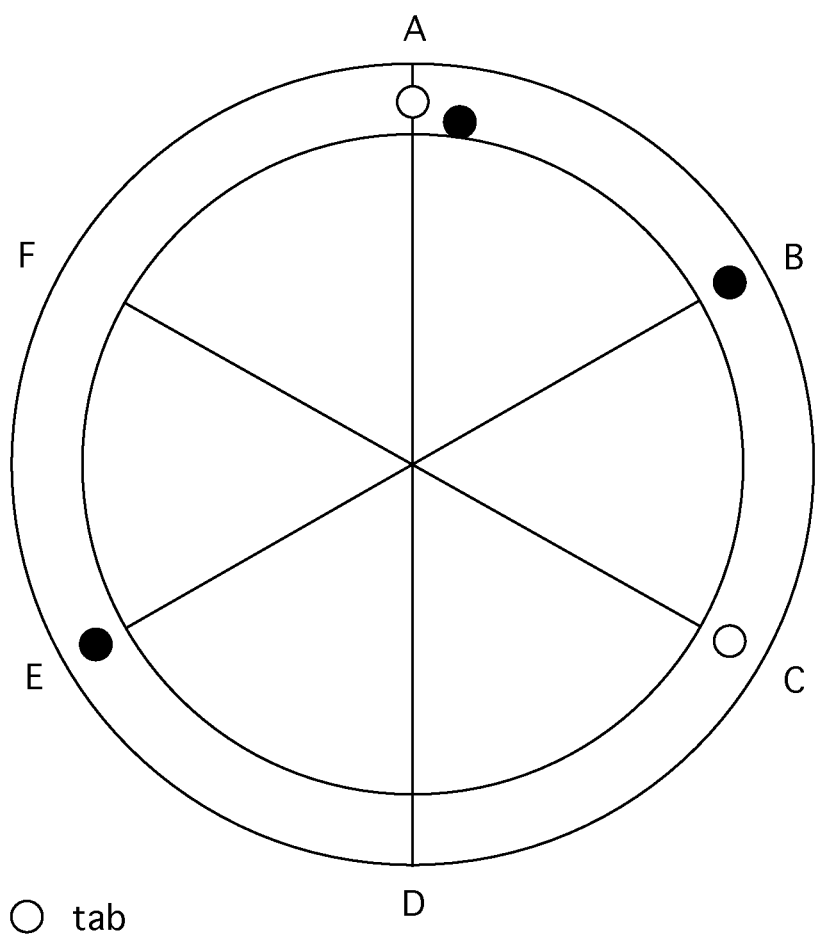
Figure 5:
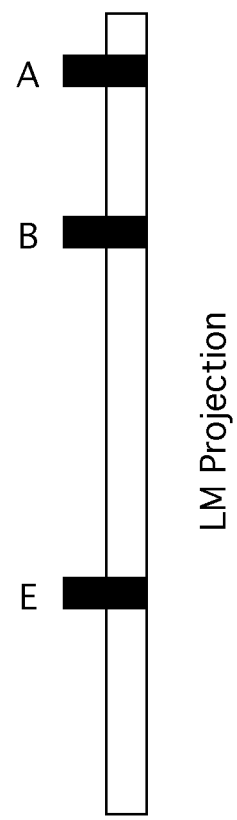

Referring now to FIG. 4, the schematic diagram illustrates an idealized x-ray image displayed on a computer screen. The x-ray of FIG. 4 is an "Anterior-Posterior" view. Another image, in "Lateral-Medial" view must accompany this image. In other words, the invention requires the availability of two images taken at a −90° angle of each other. After the surgeon designates the patient's side, which is the right side in this example (FIG. 4), the words "Lateral and Medial" and "Proximal and Distal" appear on the screen as a feature of the underlying software. As shown in FIG. 4, a round ball (visible marker) is apparent above the proximal ring away from Tab A but at precisely at Tabs B and E. Attachment locus A on the proximal ring is at the anterior of the proximal ring. In other words, due to the two-dimensional rendition of the x-ray of FIG. 4 as a representative of a three-dimensional ring, the round ball marker at attachment locus A is visible on the x-ray. The marker positioned at attachment locus B is also visible and the struts at attachment locus C do not block the marker at B; they are posterior to B. In the AP view, Tab B is anterior to Tab C. The attachment locus E poses a different problem. The struts at Tab E occupy the outer two holes of the tab and the hardware may obscure the AP view of the marker. Accordingly, the markers are placed above the proximal ring and below the distal ring. Similarly, in LM view, all three markers remain visible. FIG. 5 shows the top, AP, and LM views of the marker locations identified in this invention. This unique arrangement of markers causes all three markers to remain visible in both AP and LM view. The fact the markers at Tabs B and E fall on a diameter is not essential, just as it is not necessary to have the marker near Tab A at the same distance from the ring center as the other two markers. In fact, the invention allows the placement of all three markers anywhere around the ring. The arrangement of FIG. 5 has the merit of making the three markers visible in both AP and LM views. For convenience, throughout this specification "attachment locus" and "Tab" are used as synonyms, but it should be understood that an attachment locus may be any attachment structure or location and does not need to include a typical flange such is ordinarily referred to as a "tab." Similarly, at Tab E of the proximal ring of FIG. 5, which falls posterior to Tab F in the AP, has a marker to reveal it on the x-ray image. On the distal ring, Tabs A and E are free but Tab B resembles Tab E of the proximal ring because it must accommodate two struts and a ball marker. In conclusion, Tabs A and B are on the anterior of the proximal ring and are visible on the AP view. The marker at E is visible because it points proximally (above the ring) and Tab F does not obscure Tab E. The markers at Tabs B, A, and E of the distal ring are likewise completely visible because they point distally and Tabs A and E are free of struts. Therefore, the presence of three markers on each ring provides a position orienting marker when the three dimensional rings are rendered in two-dimensional x-ray or other imaging.

The goal of using the x-ray or similar image in FIG. 4 (together with at least one second x-ray or other image described below) is to establish a base line, mathematically expressed, to describe the positional status of the rings, struts and bones. As a matter of geometry, it is necessary to locate the centers of both the proximal and the distal rings. In addition, it becomes necessary to account for the angulation of the bone(s) and of the rings with respect to the Cartesian coordinate system. Therefore, in the preferred embodiment of the invention, the initial x-ray, in the example of FIG. 4, should show the attachment locus A centered in the middle of the proximal ring. This means that point A is at the origin of the LM plane (AP plane), whereas a line drawn between marker E and marker B defines the slope of the proximal ring in the AP view and gives an estimate of the pitch (rotation about AP line). If the marker at A falls on the EB line, we conclude that the pitch angle that the ring makes is zero. Otherwise, the algorithm computes this pitch angle from the AP data and the roll angle from the LM data. Likewise, a line between marker E and marker B defines the slope of the proximal ring in the LM and gives an estimate of the roll (rotation about LM line). In viewing FIG. 4, those skilled in the art will appreciate immediately that, as a matter of geometry, it is not possible to discern three-dimensional slopes from a single two-dimensional x-ray or other any two-dimensional image.

Before moving on to other images generated from a different angle, however, those practicing this invention will realize that the present invention embraces the use of x-ray images on computer screens outfitted with drawing software. The user draws lines on a screen and identifies specific points and the program registers these actions and extracts coordinate and other information for subsequent computation of strut lengths to affect bone repositioning. Usually the user is human, although a robotic user can also use the present invention.

Figure 6:
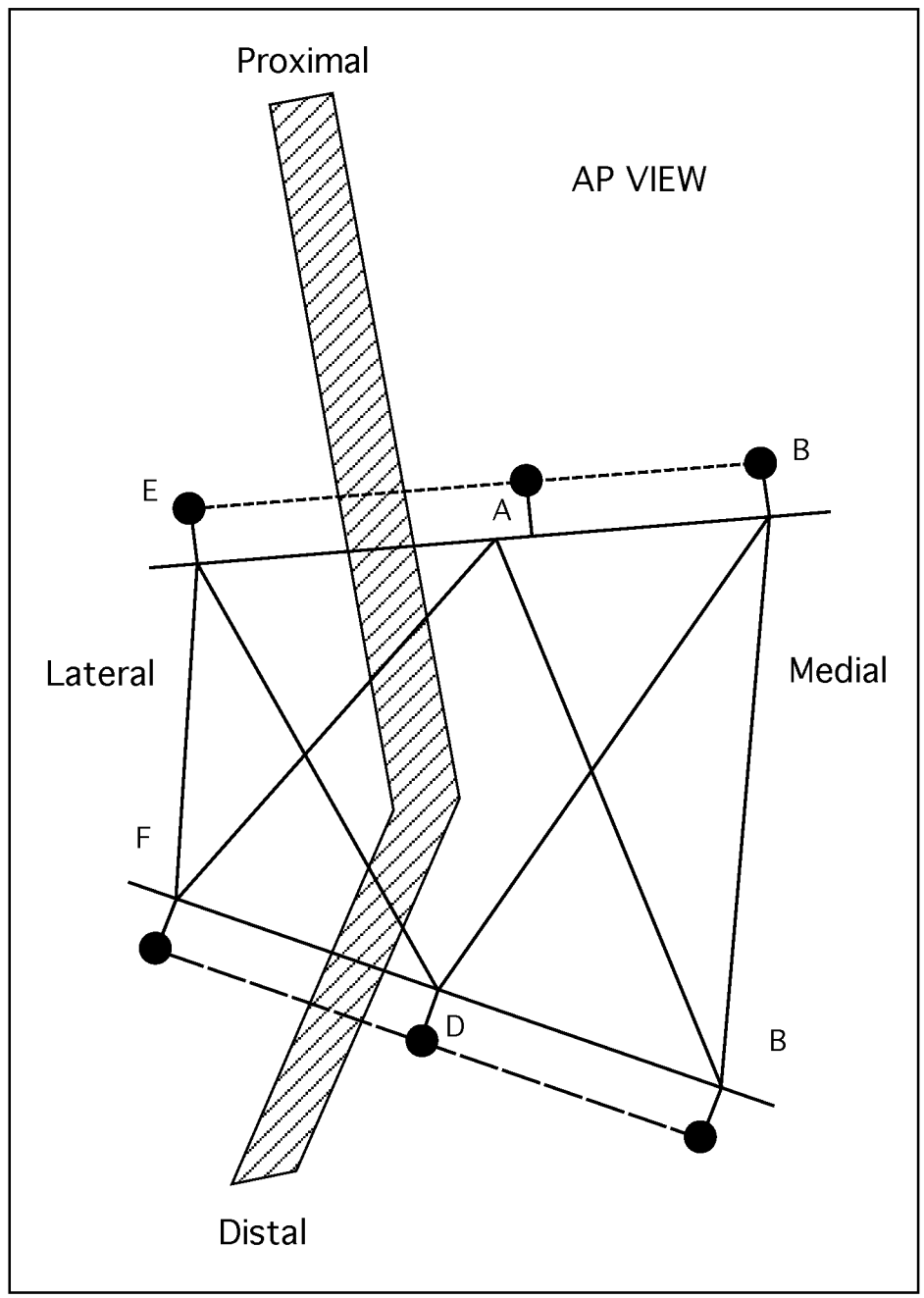
FIG. 6 is a schematic diagram of an idealized x-ray image displayed on a computer screen.

FIG. 6 illustrates the literal drawing of a line between the marker at position A and the markers at positions E & B on the proximal ring. In the previous paragraph, we described the theoretical generation of these lines. The user actually employs a computer mouse to draw a line, in this case between E and A and B on the proximal ring. The user draws additional lines on the same x-ray image as shown and connects Tabs F and D, and Tabs D and E, on the distal ring. The lines appear in yellow.

Figure 7:
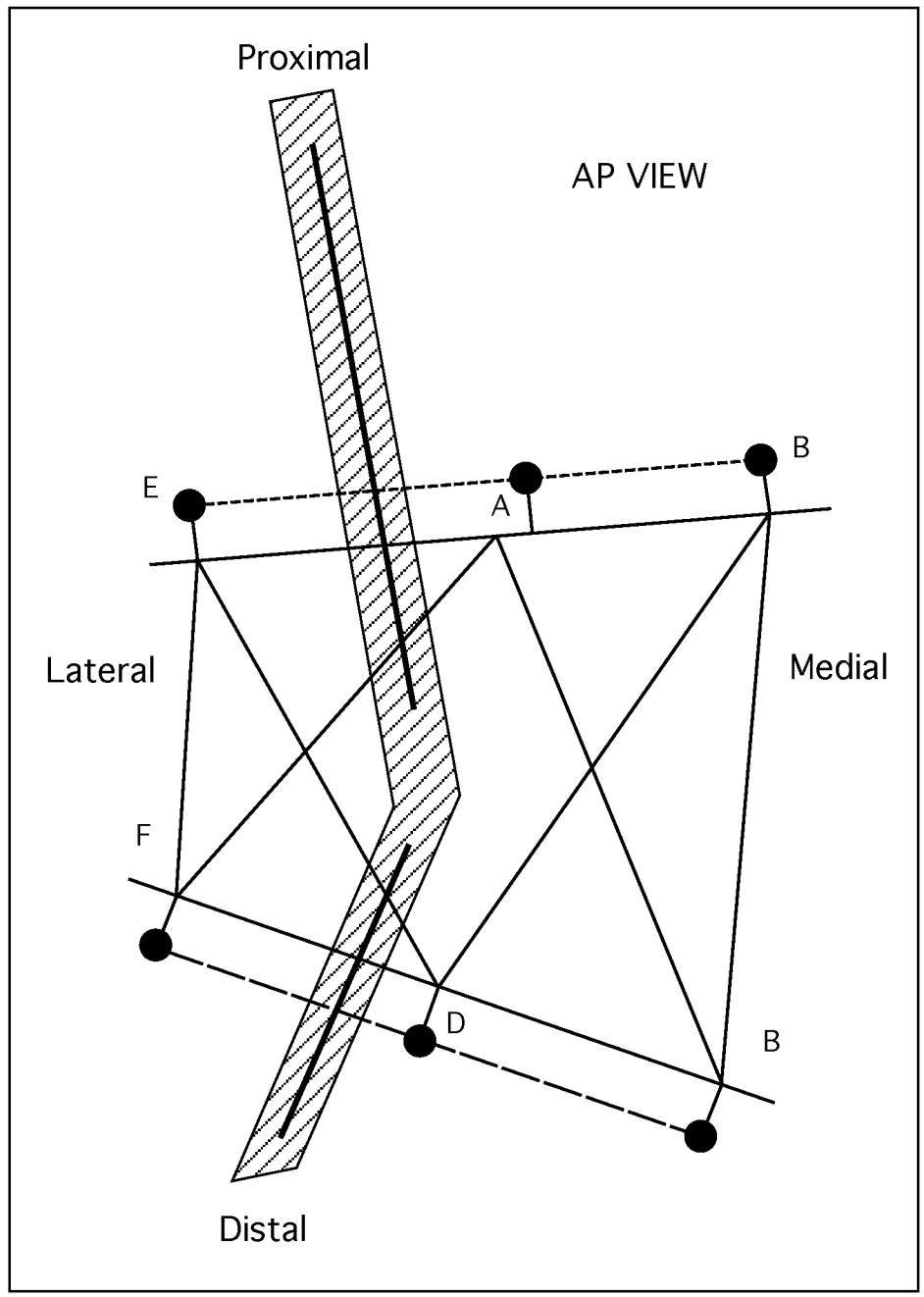
FIGS. 7-10 are schematic diagrams of idealized x-ray images displayed on a computer screen, in which a health care practitioner has marked lines showing the angles of the bones on each computer display.

Referring now to FIG. 7, the user draws one line on the proximal bone of the x-ray image on the screen, proximal to distal, parallel to the bone in the view, and a second on the distal bone, distal to proximal, parallel to the bone in the view. The lines appear in white against the gray bone background.

Figure 8:
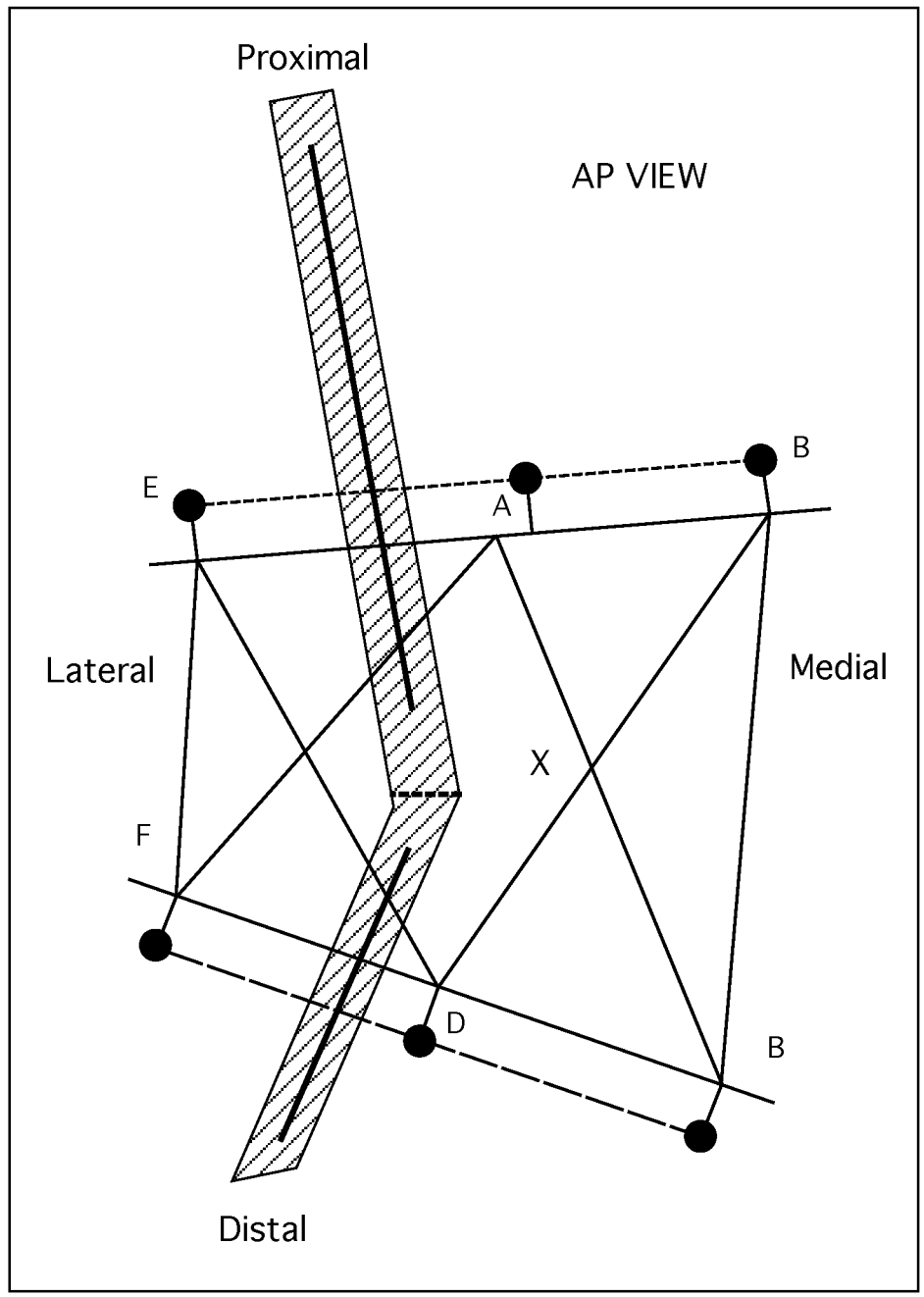

Referring now to FIG. 8, the next sequential step (using the same image on the screen as shown in FIG. 7) is to draw a line to identify the osteotomy position anticipated or executed and to click the mouse at two points on that line. The line appears in red. In the same FIG. 8, the user marks with the letter "X" the proposed center of rotation and angulation (CORA) pivot point for the moving ring.

Figure 9:
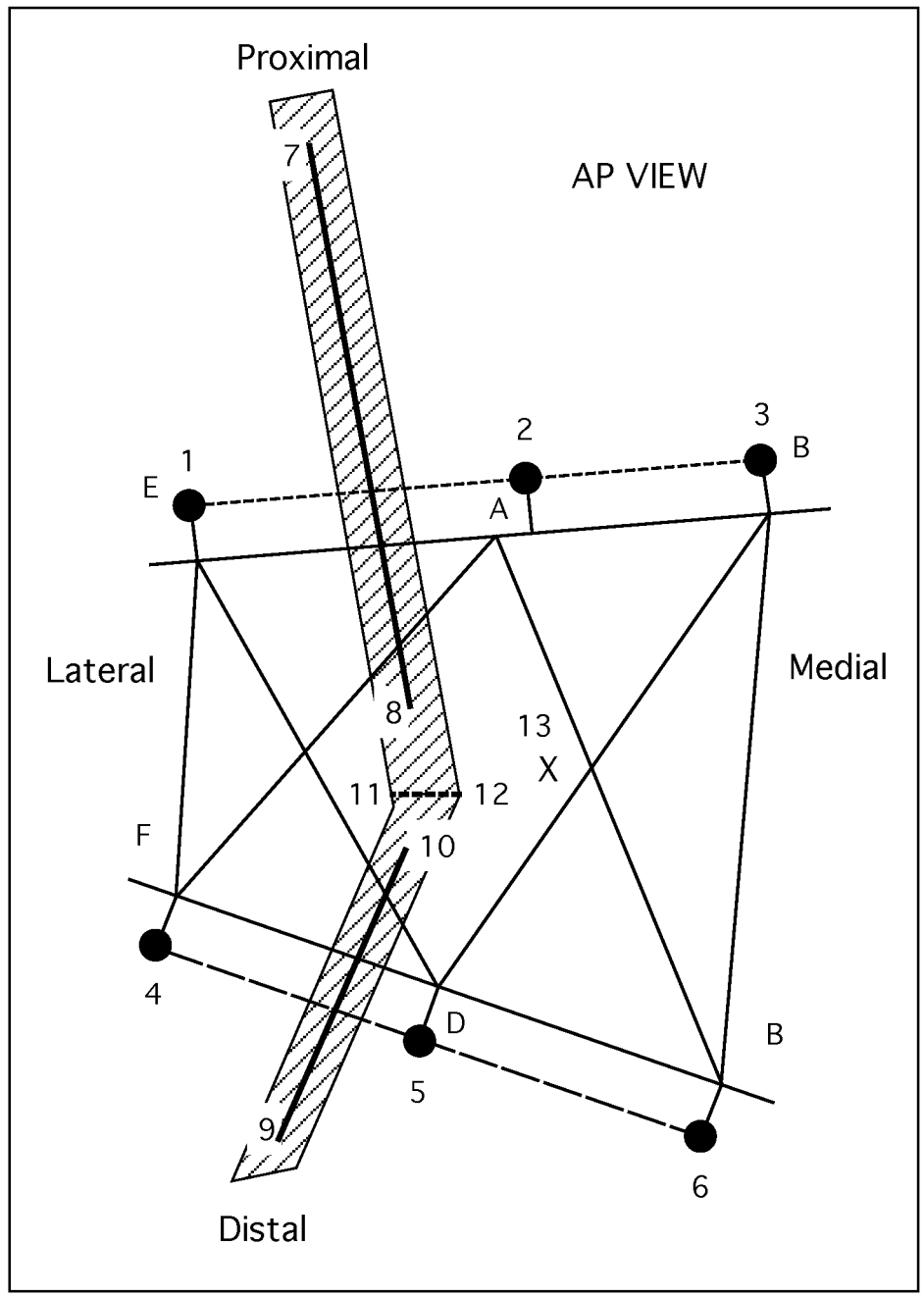

Referring now to FIG. 9, each line endpoint shows a unique numerical identifier for reference only.

Figure 10:
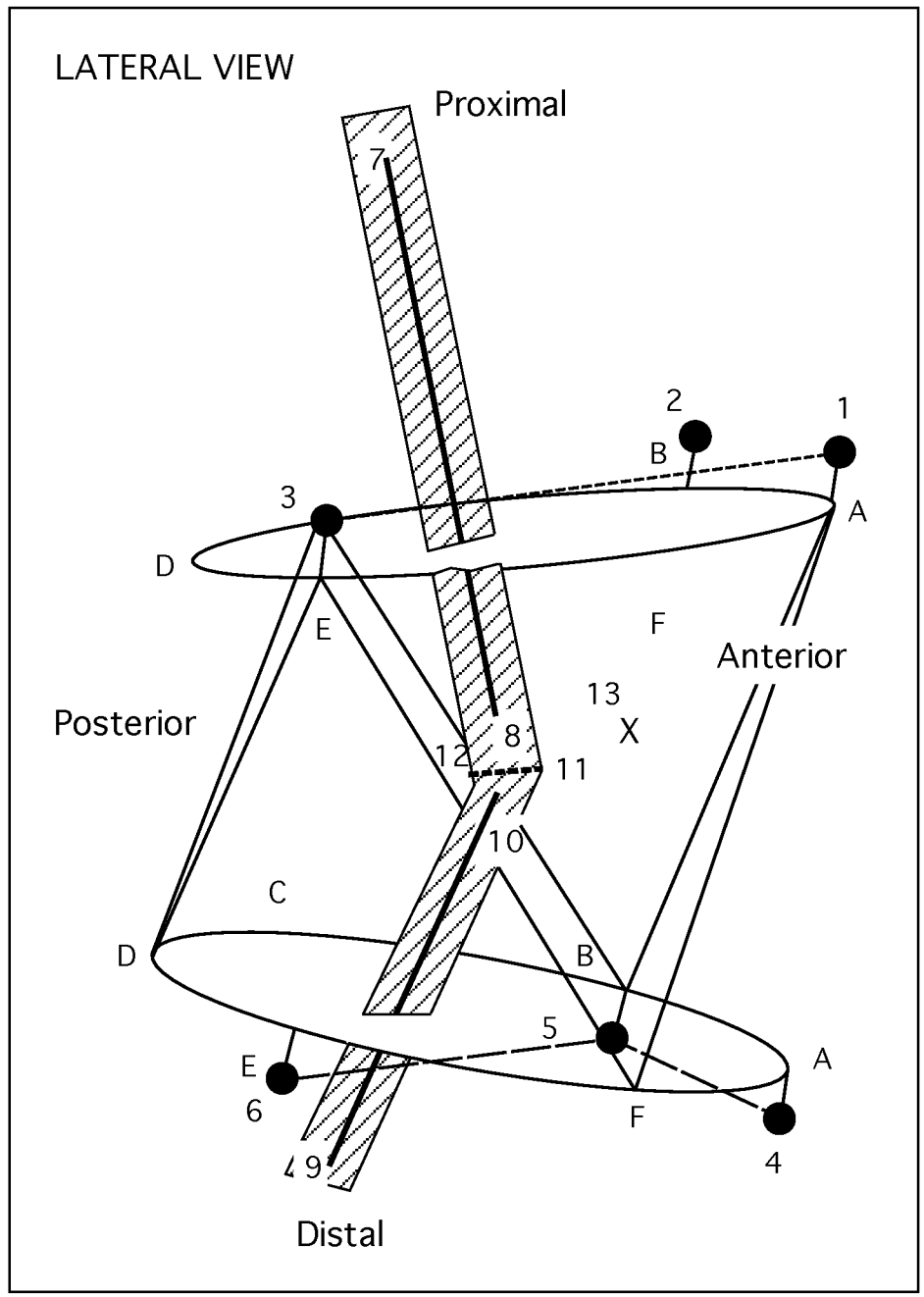

In FIG. 10, the user repeats the same P&C steps for LM view as described above for the AP view, which resulted in FIG. 9. Because neither ring is perpendicular to the proximal-distal axis, the rings appear as ellipses to account for the individual pitch and roll angles.

Figure 11:
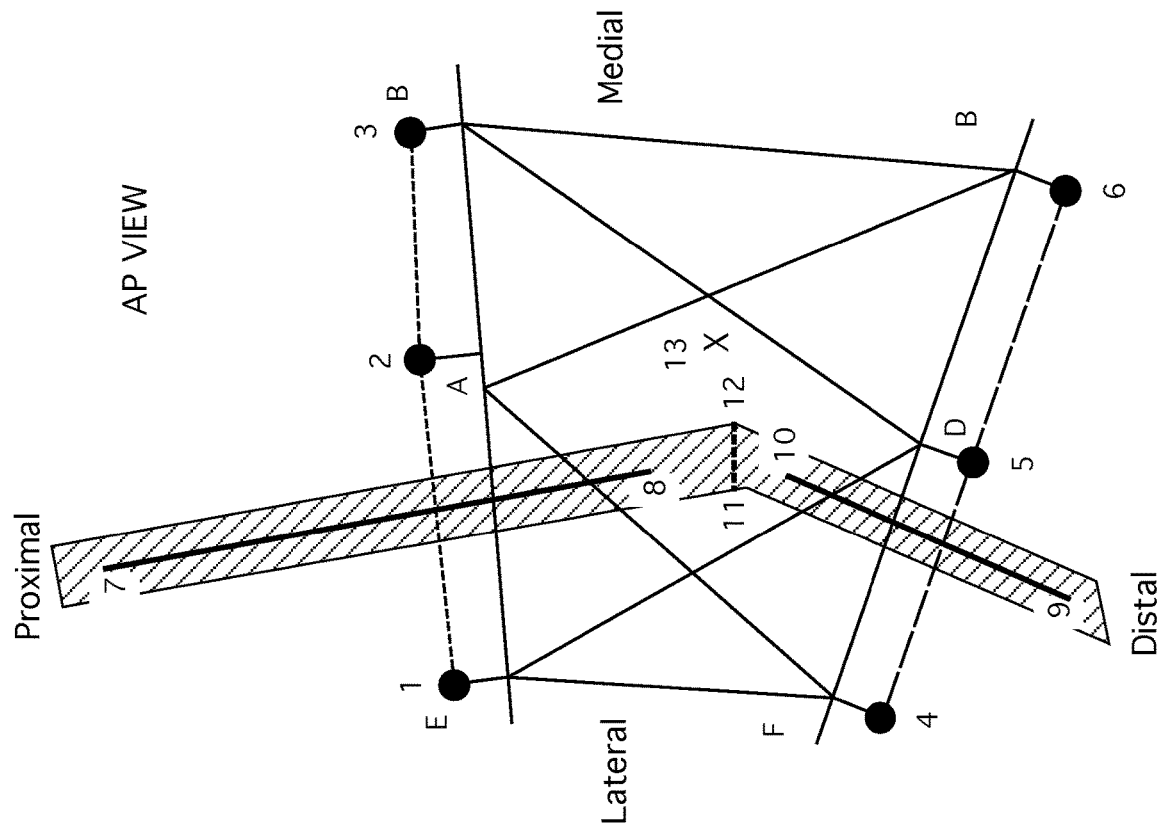
FIG. 11 is a schematic diagram of an anterior-posterior x-ray image displayed on a computer screen, together with the applicable slope calculations for the slopes shown therein.

FIG. 11 then defines the angles $\lambda_{p1}, \lambda_{p2}, \lambda_{d1}$, and $\lambda_{d2}$ made by the rings and bones with their respective horizontal axis. These angles therefore show all the points, lines, and angles necessary to position and to track the structures in the AP view.

For the proximal ring, $$\text{Slope} = m_{p2} = \frac{z_2 - z_1}{x_2 - x_2} \text{angle} = \lambda_{p2} = \tan^{-1}(m_{p2})$$

For the proximal bone, $$\text{Slope} = m_{p1} = \frac{z_8 - z_7}{x_8 - x_7} \text{angle} = \lambda_{p1} = \tan^{-1}(m_{p1})$$

For the distal ring, $$\text{Slope} = m_{d2} = \frac{z_5 - z_4}{x_5 - x_4} \text{angle} = \lambda_{d2} = \tan^{-1}(m_{d2})$$

For the distal bone, $$\text{Slope} = m_{d1} = \frac{z_9 - z_{10}}{x_9 - x_{10}} \text{angle} = \lambda_{d1} = \tan^{-1}(m_{d1})$$

The compliment of the difference $(\lambda_{d1} - \lambda_{p1})$ gives the magnitude of the rotation angle to align the proximal bone with the vertical axis (proximal-distal). If either $\lambda_{p2}$ or $\lambda_{d2}$ is zero, it means the corresponding ring is not slanted relative to a line parallel to the LM axis, implying a zero-pitch angle. In any stepwise practice of the line drawing process described with respective to FIGS. 3-11, if a point is not visible on the x-ray view, then the user cannot draw the line. In such a case, the surgeon enters NA (not available) to skip the step and move on to the next step. The algorithm accounts for missing information internally. The angle between the proximal and distal rings is the difference $(\lambda_{p2} - \lambda_{d2})$ for the LM view produces the angles that the rings and bones make with the AP axis. It should be obvious that if the yaw angle of a ring is zero, then any linear translation of the ring leaves the distances $(x_2 - x_1)$ and $(x_2 - x_3)$ unchanged. Because the location of the markers is known in advance, the exact values of $(x_2 - x_1)$ and $(x_2 - x_3)$ are also known. Thus, in the absence of yaw, the measured distances ($x_2-x_1$) and ($x_2-x_3$) can give a measure of the ring diameter, and hence the scale of the corresponding AP view. However, the same information can provide the yaw angle if the scale of the image is available independently of the markers. By placing an object of known dimensions, such as ruler, a disc, a ring or ball, during the taking of the x-ray, we can realize an independent scale for the image. The distance between the extreme ends of the ring, when visible on the computer screen, provides an exact measure of the outside diameter of the ring. Thus, if the ring possesses a uniform diameter and does not include protrusions on an otherwise uniform ring, its x-ray or other image will always give the outside diameter regardless of any angulation, yaw, pitch or roll, or any linear translation. The outside ring diameter measurement is obtainable from pointing and clicking on the extreme ends of the ring. This measurement then provides an image scale independent of the markers and subsequently the magnitude of the yaw angle of the ring. This invention becomes more effective, if only if, the outside of a ring is perfectly round. It follows that the ring must contain two series of openings, inner for the positioning of fixation hardware to secure pins and wires, tensioned and not tensioned, and another set of openings for the creation of "virtual" tabs for the efficient placement of the struts as required in a Stewart Platform implementation.

Figure 12:
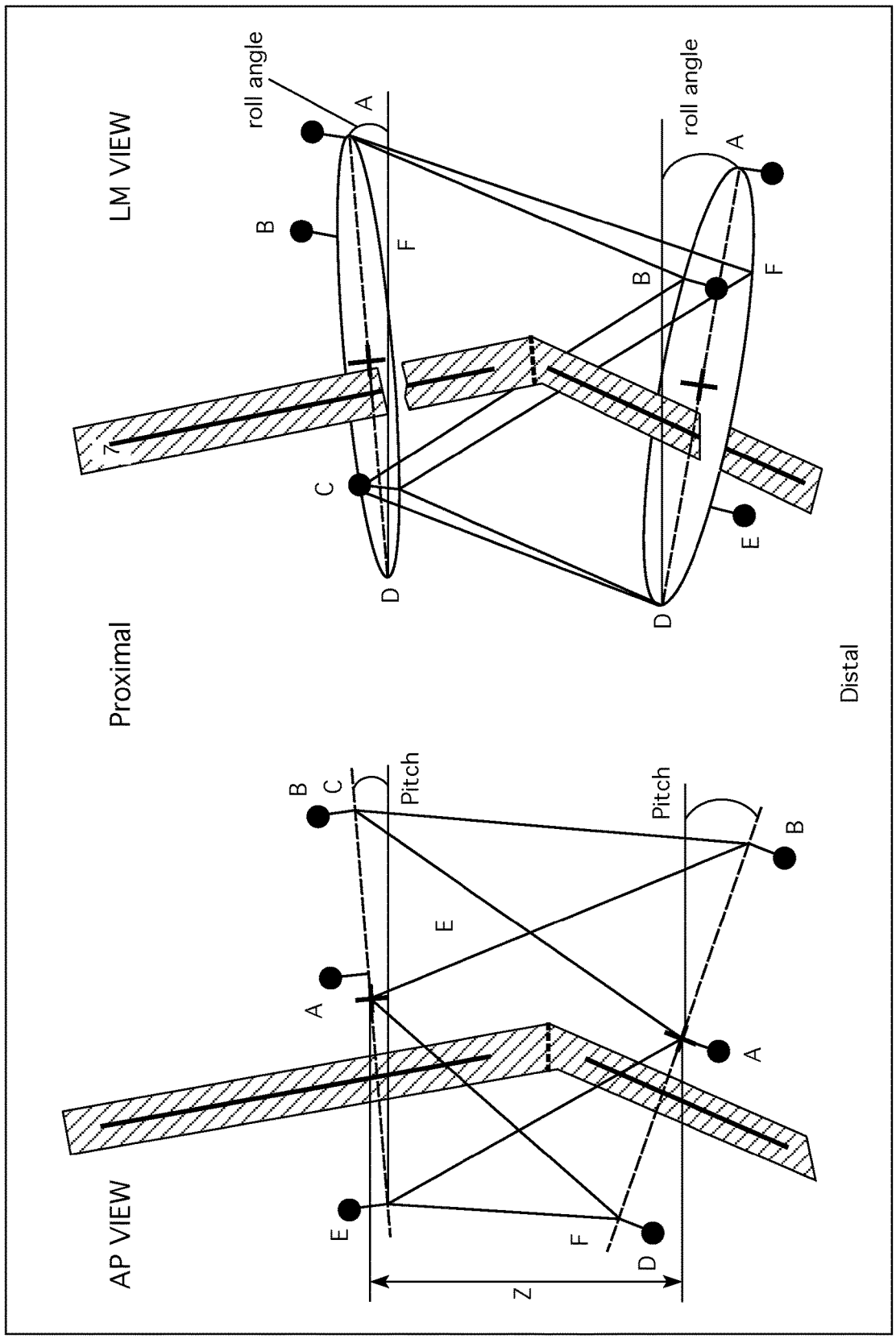
FIG. 12 is a two-part schematic diagram which illustrates how the present invention produces measurements of yaw, pitch and roll.

Furthermore, the center of the line drawn between the extreme ends of a ring gives the center of the ring in that view, AP or LM. Once the center of each ring becomes available known in both the AP and LM views, the proximal-distal distance between the ring centers becomes available. FIG. 12 illustrates how the P&C implementation produces the following measurements: coordinates of the centers of each ring with respect to a Cartesian coordinate system with an arbitrary origin, and the individual ring angles (yaw, pitch and roll) with respect to the coordinate axes. The program requires two views and the placement of at least three markers at known locations on each ring. The algorithm assumes that the two scales are not necessarily equal. In addition, the two views must share certain features. The vertical distance between the two ring centers in the AP view should equal that in the LM view after scaling. Similarly, the vertical coordinates of the osteotomy and CORA must match in the two views. The program accounts for possible measurement errors and adjusts the scales in order to minimize these errors. FIG. 12 illustrates these features. After scaling is complete, it is possible to populate all values for all three-dimensional calculations from the combined AP and LM views. This information feeds seamlessly into the algorithm to compute the magnitude of the strut adjustments to affect surgical objectives.

A goal of the present invention is to take known geometry and kinematics calculations, such as those exemplified above, and render them as an algorithm embodied in a computer. The data are extracted from lines drawn on a computer screen based on x-ray or other images depicted from at least two angles normal to one another. The hardware shown in the images may include static sensors or other detectors that identify the position and orientation of the rings in real time. The struts may incorporate motors controlled by a digital controller, essentially a special purpose computer, to affect strut length adjustment automatically. In other words, automated repositioning of the hardware occurs following commands generated from the lines drawn on the screen (overlaying the images on a computer screen) and data extracted from these lines drawn. The process proceeds seamlessly from pointing and clicking on an image to the repositioning of hardware and bone fragments with minimal manual interference. The communication between the controller and the motor can be direct, hard wiring or wireless. The source of power can be a chargeable battery imbedded within the strut or from an external electric or another power source. The invention therefore inheres in the combination of at least one computer, imaging rendition equipment having at least one screen, with the screen being adapted to receive drawing lines from the user and concomitant drawing software. The invention also includes the algorithms for calculating bone and structure position together with an output to a user. The struts may incorporate motors controllable from a programmable computer and should include digital or other readout of the strut length. The ring platforms must be circular, of known outside diameter, and void of any discernable protrusion.

Regarding the markers, when they are visible in the views they facilitate orientation and positioning that can be confusing when the markers are not present. The inclusion of at least three markers on each ring enhances the ability to view the ring positions on the screen images. Knowledge of the position of the markers influences the forward solution of the Stewart Platform problem. For example, it is possible to use the positions of the markers on the rings as obtained from the P&C process to introduce three lengths that the computational model must reproduce. Any deviation between the actual and computed lengths will be treated as errors to be corrected by modifying the translation and angular coordinates of the moving ring just as we do with the six strut lengths. Thus, in the AP view, we have three lengths involving only x and z; in the LM view, we have another three lengths involving y and z. There is a definite relationship between the x- and y-coordinate values dictated by the position of the markers on the rings; that is, the three angles and three distances from the ring center. If the z-coordinate of the marker at a given position exceeds the marker height, the view indicates proximal ring rotation about the x- and/or y-coordinate. It is conceivable that only one marker on the proximal ring is visible. Whatever is visible can confirm the rotation of the ring about the AP or LM axis. Similarly, we can discern the angulation of the distal ring. Most import though is the fact that we can forgo the markers at Tabs B & E in favor of a single marker at Tab A.

Figure 13:
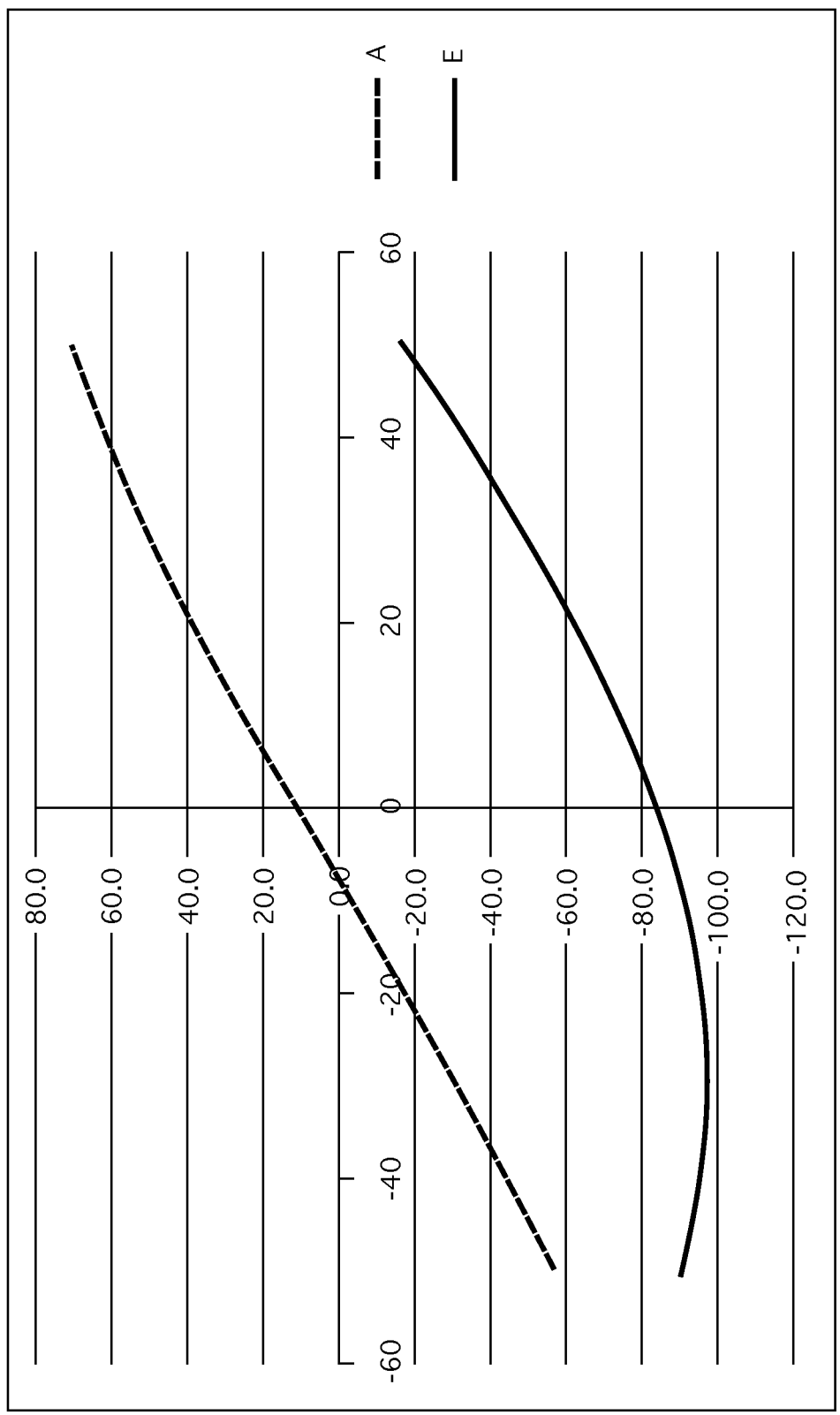
FIG. 13 is a line graph showing the angle variations of FIG. 12 in line graph format.

By way of synthesizing the above, then, from the AP view, we have derived two of the coordinates of the distal ring center (x and z) and the inter-ring pitch angle, ($\lambda_{p2}-\lambda_{d2}$). The LM view provided us with the y-coordinate of the distal ring center and the inter-ring roll angle. We still need an estimate of the yaw, the rotation angle of the rings about the z-axis. It is possible to determine the yaw angle from the AP view. Tab A of the distal ring and Tab D of the proximal should fall along a vertical line if the yaw angle is zero and the two rings are not displaced along the LM and AP axes. We have modeled the tab coordinates of the two rings in the absence of a pitch or roll angle. The computer algorithm provides a procedure to estimate the yaw angle of each ring about its z-axis. The coordinates of each marker vary uniquely from the other two as the magnitude of the yaw varies. FIG. 13 shows the x-coordinate of the Tabs near A and at B as the yaw angle varies from −50° to +50°. In the example of FIG. 13, the marker at is at hole #2 of the inner holes of a 155 mm ring. The variation in the AP view differs from that of the LM view. Thus, the markers even when only partially visible help to define all the critical parameters, which define the geometry of the two rings with respect to each other.

If we assume that all data extracted from the AP and LM views are scaled properly, there remains the issue of the origin of the coordinate system. Our approach does not require the user to designate the origin. The P&C data reference is what the programmer of the drafting program designates. For RPS, we have used the convention that the origin of the proximal, i.e. reference, ring as the zero point. However, the two views must correspond to the same physical object portrayed by the two x-rays. Any point that is common to both the AP and LM views will end up with two z-coordinate values that most likely differ from one view to the other. Logic suggests we average the two values. After we define the origin, we translate the origin of the image to the center of the proximal ring. The user is not involved in these manipulations. We then rotate the entire image in both views such that the proximal ring lies along the LM axis. This may cause the bone to change its orientation but will not necessarily cause the proximal bone segment to be parallel to the new Proximal-Distal axis, i.e. z-axis. We can affect this change and present it to the user any time we display an image for evaluation. Alternatively, we could rotate the entire image such that the proximal bone is along the z-axis. However, the proximal ring will appear angled with the LM axis, unless the user had placed it perpendicular to the bone axis.

The present invention also embraces a number of surgical and clinical accessories and devices as described and depicted below. An accessory feature to the invention is vibration-free struts with direct "length reading." As described above, orthopedic surgeons utilize external ring fixators to position bone segment, correct limb deformities, and lengthen limbs. The fixator consists of rings connected with six adjustable struts to provide stability and allow six degrees of freedom manipulation of one ring relative to the other. In a three-dimensional coordinate system, the degrees of freedom are the x, y, and z-coordinates of the center one ring (moving) with respect to the other (reference) and three angles of yaw, pitch and roll corresponding to the rotation of the mobile ring about the z-, y- or x-axis respectively. The Taylor Spatial Frame, or TSF, is essentially the utilization of the Stewart Platform in an orthopedics. This disclosure pertains to a new adjustable strut that has enhanced efficiency and superior performance to struts of the prior art.

An ideal strut has a number of required characteristics as to its mechanics. The first requirement is for rapid "free movement" adjustment. During the process of attaching the spatial frame to the patient's limb and afterwards, the frame must be easy to manipulate manually without offering much resistance. If the frame is pre-assembled before the surgery, the surgeon may need to make quick adjustments of the position of the rings with respect to each other in order to position the bone in a particular orientation with each other. If the rings are already attached to the patient bones, the surgeon must attach the struts, one a time, and the struts require free and easy adjustment of each strut to match the distance between the rings where each strut attaches. Once in position, the surgeon disables the quick-adjust feature by tightening a screw, a bolt or another device to prevent strut motion while the patient goes about her daily chores. Second, for the duration of the treatment, it is necessary to adjust the length of each strut periodically in order to reposition the bone segments. The adjustment takes place over time at a rate consistent with the bone's ability to regenerate, approximately 1 mm per day. Fine, daily adjustment in ½ mm (or ¼ mm) increments is often necessary. After each adjustment, a locking mechanism is necessary to prevent the strut from changing length for whatever reason. The strut must also withstand the daily activities of the patient without loosening. Third, over the course of the treatment, the strut length may have to change beyond the range of adjustment of the strut length. This situation requires swapping individual struts for different sizes, shorter or longer. Fourth, the strut must possess adequate strength to withstand the actions of daily living of the heaviest patient with minimal deflection and absence of a catastrophic failure. Fifth, in the course of deformity correction, the struts may have to be angled almost 90° with respect to the rings. In deformity cases, it is necessary for the strut to possess a large angular range of movement at the joints at each end. Typically, the range 40° from vertical, 360° around, is the minimum requirement. Sixth, and finally, any looseness in the axial direction will cause the rings to move slightly relative to each other in the course of the patient's daily activities. The vibration hinders the healing process and is to be avoided whenever possible. In terms of surgeon/patient/device communications, beyond simple mechanics, both the surgeon and the patient require a clear ruler scale showing the strut length at all times. This simplifies the surgeon's interaction with the software used to generate the daily correction schedule. In addition, numerical- or color-coding assists the communications. For simplicity of use, an indicator of the nominal direction of rotation of the fine adjustment nut is extremely helpful.

An ideal strut also possesses the following secondary characteristics:
  No change in length as the strut changes angle;
  Additional angular range of movement at the joint up to 90° from vertical;
  Lightweight; visually appealing;
  Easy to read markings for strut coding and read out of strut length;
  High adjustment efficiency, otherwise known as maximizing the allowable adjustment relative to the unexpanded strut length, which eliminates the need to change struts in midstream while still having a large range of travel, and accommodates especially large corrections;
  Easy rotational movement of the joints, making it easier to attach the struts to the rings;
  Ability to lock the rapid-adjust "permanently" to prevent the patient from tampering with it, and interfering with the correction.

Figure 14:
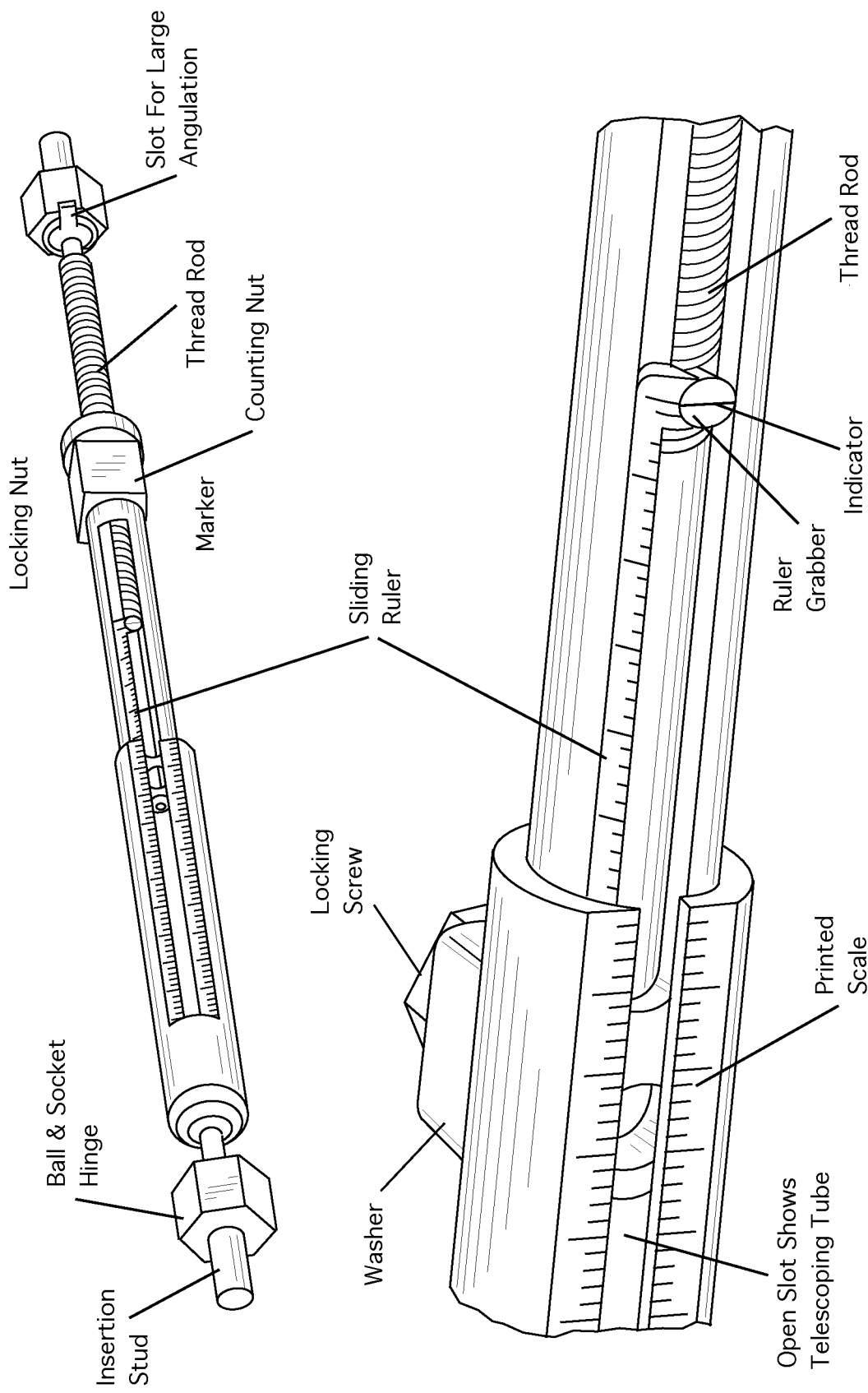
FIG. 14 is a perspective view of an ideal strut for use in the present invention, in full perspective and detailed view showing the "ruler grabber.

In order to meet the above criteria, the present invention embraces an improved strut as follows. FIG. 14 is a computer-generated sketch of the strut, which is the subject of this invention. The strut body is an aluminum tube open on one end and closed on the other end, attached to a hinge. The hinges at each end of the strut are ball-and-socket type. The strut body has a slot on one side to reveal a pointer, which points on a scale printed on the body. Within the body, a telescoping tube slides freely. A screw on the opposite the pointer secures the telescoping tube to the strut body. My loosening the screw, the user can adjust the length of the struts quickly by sliding the tube in and out of the strut body. The sliding inner telescoping tube fulfills the quick-adjust requirement of the strut. The telescoping tube is smooth on the outside and is threaded on the inside to accept a threaded rod of matching pattern. A counting nut mounted on the end of the telescoping tube controls the advance of the threaded rod and hence, the strut length. The counting nut turns in increments of ½ or ¼ turn and stops. A threaded locking nut mounted on the threaded rod between the counting nut and the hinge locks the struts after any adjustment to prevent spurious displacements.

The counting nut mechanism provides smooth, incremental strut length adjust. The combination of a telescoping tube and a threaded rod within it achieve the desired objective of high ratio of expanded strut length to its non-extended length. The non-expanded strut length consists of the combination the strut body and the hinges. The sliding quick-adjust telescoping tube provides possible range almost equal to the length of the strut body. The threaded rod when fully extended provides yet a second length increase slightly less than the length of the telescoping tube. The user can achieve any length ranging from totally non-extended to totally extended in any combination of quick-adjust and incremental fractional turn. While the length indicator is anywhere within the strut body, its position points to the ruler and indicates the strut length, defined as the distance between the centers of the balls of the two hinges. However, once the strut expands causing the indicator to exit the strut body (outer tube), it can no longer point to the scale printed on the strut body. It is possible to print another ruler scale on the telescoping tube. The motion of the telescoping tube exposes this new ruler. However, it is not possible to devise a scale, which provides the overall strut length, or the distance between the centers of the balls of the two hinges. This invention addresses this requirement by incorporating a sliding ruler, which remains hidden and out of view as long as the telescoping tube is residing totally within the strut body. When the strut expands by whatever mechanism causing the indicator to reach the edge of the tube body, the sliding ruler and the indicator couple to each other causing the ruler to travel in tow with the indicator as the strut expands. When the strut contracts, the indicator with the sliding ruler attached to it eventually returns to the edge of the strut body. After the telescoping tube returns completely to its non-expanded position, further reduction in strut length cause by turning the counting nut causes the indicator to disengage from the sliding ruler, which cannot travel backward beyond that point. Further reduction in length does not involve the sliding ruler.

Referring to FIG. 13, the strut body and the telescoping tube are made from high strength aluminum, anodized and laser etched as desired. The ball and socket material is aluminum or any convenient material. The ball surface is mirror-polished. A high molecular weight polyethylene, HMWPE, washer separates the ball and sockets and allows the free movement of the ball in the socket and eliminates parasitic motion inherent in a universal hinge. We form the hinge by crimping the socket over the ball to a precise tolerance to insure joint integrity without restraining the motion. The insert studs and the threaded rod are stainless steel. The counting nut is aluminum or stainless and the locking nut is aluminum, anodized in different color to provide each strut in a set of six with a unique color. The locking screw and washer are either aluminum or stainless. All threaded components are M6, metric 6 mm thread diameter and 1.0 mm pitch, to match the industry worldwide standard hardware for external fixator.

Another accessory and complementary technology embraced by this patent application is the motorization the struts. A step motor, with the inside of the motor rotor threaded to function as a counting nut, provides a mechanism for electrically adjusting the struts during the course of the treatment. A single battery, or a power supply, and an attached controller power the motors and control their individual rotation. Instead of the patient or healthcare giver making the periodic strut adjustments, the controller receives its commands from a personal computer or a similar device to make the necessary scheduled adjustment, which the RPS algorithm has generated earlier. The commands from the computer to the dedicated controller can be hard wired in the case of a computer or wireless in the case of another intelligent device. As part of this motorized application, each strut has the ability to feed back its actual length via the controller and to the personal computer. The computer checks these strut lengths and compares them to their scheduled values and then alerts the surgeon in case of a discrepancy between actual and planned values.

Figure 15:
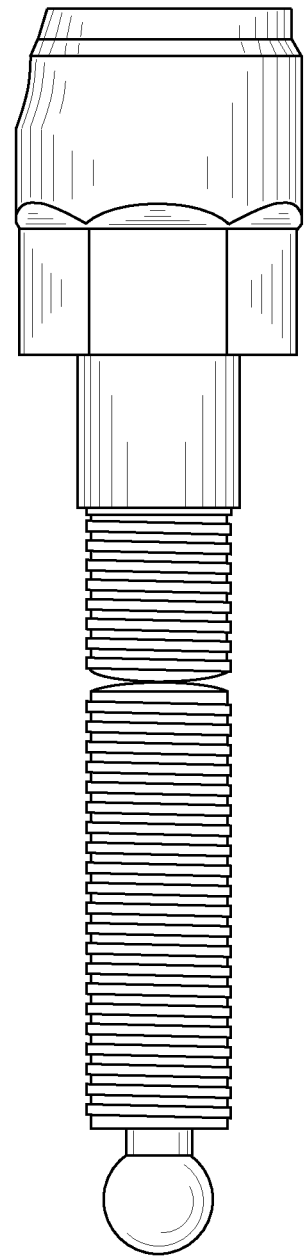
" and FIG. 15 shows adjustable ball stud markers.
Figure 15:
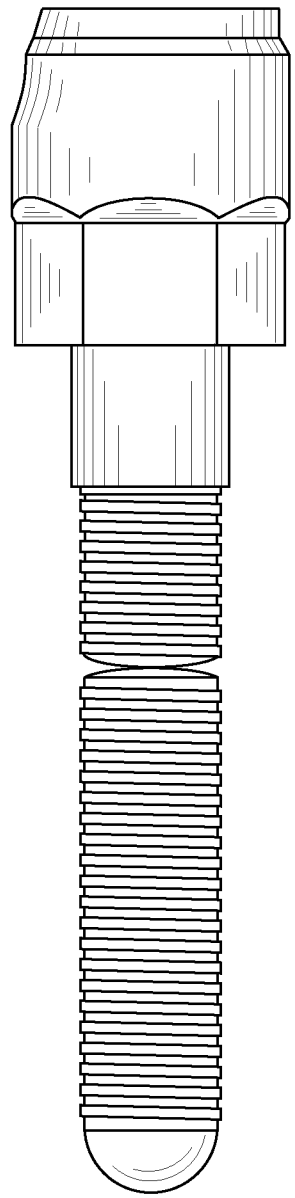

Finally, an enhancement to the above disclosure includes two additional features to the strut description. First, we add ridges to the outer tube housing as follows. When the inner tube of the strut slides out (quick-adjust extension) of the outer tube housing, it must be locked in position via a locking bolt and a washer to hold it in place and to prevent its motion when the strut is axially loaded. The bolt must be torqued heavily to secure it properly. Therefore, we added ridges on the two sides of the slit through which the locking bolt travels back and forth. The ridges are ideally 2.0 mm apart. In addition, we added two pins, imbedded into the washer. The pins fit into ridges of the outer tube housing. The result is as follows: the locking bolt prevents the washer and pins from moving radially (with respect to the tube housing) but does not support the load. The load is supported by the two pins and the ridges. We also can enhance the placement of the radiopaque markers with adjustable ball stud markers (shown in FIG. 15). In the above description, we explain the placement of independent ball studs on each ring at specific holes. One ideal midpoint for such a placement is generally the anterior midpoint of the ring. Typically, though, a strut already occupies this location, and often a half-pin holder sits between the two struts. Therefore, the adjustable ball stud marker resides in an extended shaft to accept the "ball" as follows. If we extend the threaded ends of the strut where it attaches to the ring, we can machine a ball marker in the thread end or screw a ball onto the thread past the nut holding the strut to the ring. This enables completely free choice of placement of the ball marker at the desired or optimum location, not just at a hole or location on the ring that otherwise happens to be free.

What is claimed is:

1. An apparatus for external placement of a bone of a limb using an adjustable strut, comprising:
   a circular platform having an open center adapted and configured for placement therethrough of a limb, the open center having an inner diameter, said circular platform having an outer circumferential surface spaced apart from the inner diameter, said circular platform having a top surface and a bottom surface, said circular platform having a width extending between said top surface and said bottom surface and located between the inner diameter and the outer circumferential surface, said circular platform including a plurality of holes each adapted and configured for attachment to an end of an adjustable strut, each of the holes extending through the width, said circular platform including a plurality of slots each adapted and configured for attachment to an end of an adjustable strut, each of the slots extending through the width, the plurality of holes being located along a first diameter greater than the inner diameter, and the plurality of slots being located along a second diameter greater than the first diameter;
   three separable position markers located on said circular platform and supported at different respective positions spaced apart along said circular platform, at least one of said position markers located on a different diameter of said circular platform than said two other position markers; and
   a computer including a computer screen and being adapted and configured to:

extract position data from at least two x-rays or other orthopedically significant images of said circular platform, create a representation of the x-rays or images on said computer screen based on said position data, calculate an adjustment to a relative placement of said circular platform based on said position data, and display on said computer screen adjustment data pertaining to said adjustment.

2. The apparatus of claim 1 wherein the plurality of holes are a first plurality of holes, and said apparatus further comprising a second plurality of holes interspersed within the plurality of slots along the second diameter.

3. A Stewart Platform for supporting two adjacent bone fragments, comprising:
- a first platform having a first plurality of holes and a first plurality of slots being intermixed with the first plurality of holes, said first platform being adapted and configured to be connected to a first bone fragment;
- a second platform having a second plurality of holes and a second plurality of slots being intermixed with the second plurality of holes, said second platform being adapted and configured to be connected to a second bone fragment;
- a first strut and a second strut, each said strut having two ends each adapted and configured for fixation to either one of said holes or one of said slots, one end of said first strut being fixed to a hole of said first platform and the other end of said first strut being fixed to a hole of said second platform, and one end of said second strut being fixed to a slot of said first platform and the other end of said second strut being fixed to a slot of said second platform;
- a first three separable position markers located on said first platform and supported at different respective positions spaced apart along said first platform, at least one of said first three separable position markers located on a different diameter of said first platform than said two other of said first three separable position markers;
- a second three separable position markers located on said second platform and supported at different respective positions spaced apart along said second platform, at least one of said second three separable position markers located on a different diameter of said second platform than said two other of said second three separable position markers; and
- a computer including a computer screen and being adapted and configured to:
  - extract first position data from at least two x-rays or other orthopedically significant images of said first platform,
  - create, based on said first position data, a representation on said computer screen of the at least two x-rays or other orthopedically significant images of said first platform,
  - calculate, based on said first position data, an adjustment to a relative placement of said first platform,
  - display on said computer screen first adjustment data pertaining to said adjustment to said relative placement of said first platform,
  - extract second position data from at least two x-rays or other orthopedically significant images of said second platform,
  - create, based on said second position data, a representation on said computer screen of the at least two x-rays or other orthopedically significant images of said second platform,
  - calculate, based on said second position data, an adjustment to a relative placement of said second platform, and
  - display on said computer screen second adjustment data pertaining to said adjustment to said relative placement of second platform.

4. The Stewart Platform of claim 3 wherein said first platform includes a third plurality of holes, said third plurality of holes being located radially inward of said first plurality of holes and said first plurality of slots, and said second platform includes a fourth plurality of holes, said fourth plurality of holes being located radially inward of said second plurality of holes and said second plurality of slots.

* * * * *